(12) United States Patent
Koele et al.

(10) Patent No.: US 11,986,272 B2
(45) Date of Patent: May 21, 2024

(54) SENSOR PATCH HAVING A PROTECTIVE LAYER

(71) Applicant: STEADYSENSE GMBH, Seiersberg-Pirka (AT)

(72) Inventors: Werner Koele, Lieboch (AT); Peter Gasteiner, Graz (AT)

(73) Assignee: STEADYSENSE GMBH, Seiersberg-Pirka (AT)

(*) Notice: Subject to any disclaimer, the term of this patent is extended or adjusted under 35 U.S.C. 154(b) by 713 days.

(21) Appl. No.: 17/275,859

(22) PCT Filed: Sep. 12, 2019

(86) PCT No.: PCT/EP2019/074294
§ 371 (c)(1),
(2) Date: Mar. 12, 2021

(87) PCT Pub. No.: WO2020/053317
PCT Pub. Date: Mar. 19, 2020

(65) Prior Publication Data
US 2022/0039662 A1 Feb. 10, 2022

(30) Foreign Application Priority Data

Sep. 13, 2018 (DE) .......................... 102018122420.6
Jul. 22, 2019 (DE) .......................... 102019119701.5

(51) Int. Cl.
*A61B 5/01* (2006.01)
*A61B 5/00* (2006.01)

(52) U.S. Cl.
CPC .............. *A61B 5/01* (2013.01); *A61B 5/6833* (2013.01); *A61B 2562/0271* (2013.01)

(58) Field of Classification Search
CPC .. A61B 5/01; A61B 5/6833; A61B 2562/0271
See application file for complete search history.

(56) References Cited

U.S. PATENT DOCUMENTS 6,814,706 B2   11/2004   Barton et al.
9,439,599 B2*   9/2016   Thompson .............. G16H 40/67
9,782,082 B2   10/2017   Gannon et al.
(Continued)

FOREIGN PATENT DOCUMENTS

DE          60215924 T2      5/2007
DE       102009029215 A1     3/2011
(Continued)

OTHER PUBLICATIONS

International Search Report and Translation, 6 pages.
German Search Report and Translation, 15 pages.

*Primary Examiner* — Randy W Gibson
(74) *Attorney, Agent, or Firm* — Dority & Manning, P.A.

(57) ABSTRACT

A measuring device for measuring a body temperature of a living being includes a measuring unit for measuring the body temperature. The measuring device includes a first adhesive layer for fastening the measuring device on the body of the living being. The first adhesive layer is arranged at a side of the measuring device intended to face the body when the measuring device is in use. The measuring device includes a skin-compatible protective layer, which is arranged between the first adhesive layer and the measuring unit.

20 Claims, 6 Drawing Sheets

(56) References Cited

U.S. PATENT DOCUMENTS

| | | |
|---|---|---|
| 10,617,306 B2 | 4/2020 | Gannon et al. |
| 2004/0215098 A1 | 10/2004 | Barton et al. |
| 2009/0234200 A1 | 11/2009 | Husheer |
| 2011/0060206 A1 | 3/2011 | Schaaf et al. |
| 2016/0183794 A1 | 6/2016 | Gannon et al. |
| 2018/0028070 A1 | 2/2018 | Shi |
| 2018/0163095 A1 | 7/2018 | Khoche |
| 2018/0192874 A1 | 7/2018 | Koele et al. |

FOREIGN PATENT DOCUMENTS

| | | |
|---|---|---|
| DE | 102015010189 A1 | 2/2017 |
| WO | WO2014/070254 A1 | 5/2014 |

\* cited by examiner

SENSOR PATCH HAVING A PROTECTIVE LAYER

CROSS-REFERENCE TO RELATED APPLICATIONS

The present application claims priority to patent application serial number PCT/EP2019/074294, filed on Sep. 12, 2019, which patent application is hereby incorporated herein in its entirety by this reference for all purposes.

FIELD OF THE INVENTION

The present invention relates to a measuring device for measuring a body temperature of a living being, in particular of a human being, with a measuring unit for measuring the body temperature.

BACKGROUND OF THE INVENTION

DE 10 2015 010 189 A1, which corresponds to US Patent Application Publication No. 2018-0192874, which is incorporated herein in its entirety by this reference for all purposes, describes a device for determining at least one body temperature. The device includes a detection pad, which conducts body heat to a semiconductor chip, which determines the body temperature.

OBJECTS AND SUMMARY OF THE INVENTION

The problem addressed by the present invention is that of improving measuring devices from the prior art.

The problem is solved by a measuring device for measuring a body temperature of a living being, having the features described below.

The invention relates to a measuring device for measuring a body temperature of a living being. The living being can be, for example, a human being. The measuring device can be utilized, for example, for medical purposes. For example, ovulation can be determined with the aid of the measuring device. The measuring device can also be utilized, however, for unhealthy living beings and/or persons, in order to be able to monitor their state of health. The measuring device can be arranged, for example, on the skin of the living being, in order to measure the body temperature. The measuring device can be arranged, for example, at an arm or the trunk of the person. Additionally or alternatively, the measuring device can also be arranged over a wound, in order, for example, to protect the wound against dirt and in order to support the healing process.

The measuring device includes a measuring unit for measuring the body temperature. The measuring unit can include, for example, a sensor unit, with which the body temperature can be determined. The measuring unit and/or the sensor unit can include, for example, a temperature probe and/or a temperature sensor.

According to the invention, the measuring device includes a first adhesive layer for fastening the measuring device at the body of the living being. Advantageously, the first adhesive layer can also be skin-compatible. The first adhesive layer can be arranged at a side of the measuring device facing the body intended therefor. The first adhesive layer can also be arranged at the underside of the measuring device facing the body. The measuring device can be fastened at the body for a longer time with the aid of the first adhesive layer. The underside can be the side of the measuring device facing the body.

Moreover, the measuring device according to the invention can include a skin-compatible protective layer. The skin-compatible protective layer is arranged between the first adhesive layer and the measuring unit. In particular, the protective layer is therefore arranged between the skin of the living being and the measuring unit. Since the measuring unit can have, for example, a semiconductor chip, the semiconductor chip can include materials that can be injurious to health or irritating to the skin. In particular, the semiconductor chip may not have been tested to determine whether it may be used for medical purposes due to the materials contained therein. With the aid of the skin-compatible protective layer, the measuring unit does not come into contact with the body or with the skin of the living being, and so, for example, the untested semiconductor chips can also be utilized. Due to the skin-compatible protective layer, the measuring unit is encapsulated with respect to the skin. Due to the skin-compatible protective layer, an irritation, for example, due to an allergic reaction, of the skin of the body of the living being caused by the measuring unit can be avoided.

The protective layer has a thickness, and so a flow of heat between the body and the measuring unit is only slightly affected. The thickness of the protective layer can be, for example, in the range between 0.001 mm and 1 mm. For example, the protective layer has a thickness of 25 µm, 50 µm, or 75 µm.

For example, the measuring unit and/or the sensor unit can include a temperature-dependent diode and/or a temperature-dependent resistor, by means of which the body temperature is determinable.

Moreover, the measuring unit can be encapsulated, for example, by a varnish, which forms a high liquid and/or gas diffusion barrier, and so, for example, corrosion of the measuring unit can be prevented or reduced. The varnish can also be water- and/or gas-tight.

It is advantageous when the measuring device includes a heat-conducting element, by means of which a heat flow is formable between a body of the living being and the measuring unit during the use of the measuring device as intended. The heat-conducting element can therefore have thermal conductivity. A temperature difference between the body and the measuring unit can be equalized with the aid of the heat-conducting element and/or due to the heat flow, which is formable by the heat-conducting element. It is assumed that the body of the living being is much larger, i.e., has a much greater mass, than the measuring device, and so the measuring unit always assumes the temperature of the body. The temperature of the body of the living being therefore remains substantially unaffected by the contact with the measuring device. If the measuring unit has assumed the temperature of the body, the body temperature can be measured. The heat-conducting element can form the heat flow between the body and the measuring unit in both directions. This means, when the body is warmer than the measuring unit, the heat-conducting element conducts heat from the body to the measuring unit. This takes place for as long as it takes for the temperature difference between the body and the measuring unit to equalize. However, if the measuring unit is warmer than the body, the heat-conducting element conducts heat from the measuring unit to the body until the temperature difference has equalized. If the temperature of the measuring unit does not change, the measuring unit and the body have the same temperature, and so the body temperature can be determined.

Advantageously, the heat-conducting element can be arranged between the skin-compatible protective layer and the measuring unit. As a result, the heat-conducting element can exchange the heat between the body and the measuring unit. The skin-compatible protective layer is arranged between the body and the heat-conducting element during the use of the measuring device as intended. Consequently, for example, a skin irritation of the body by the heat-conducting element can be prevented. Untested materials of the heat-conducting element can also be utilized.

It is advantageous when a second adhesive layer is arranged between the skin-compatible protective layer and the measuring unit. Additionally or alternatively, the second adhesive layer can also be arranged between the skin-compatible protective layer and the heat-conducting element. As a result, the protective layer adheres at the measuring unit and/or at the heat-conducting element.

When the second adhesive layer is arranged between the protective layer and the measuring unit and/or the heat-conducting element, it is advantageous when the protective layer is designed as a double-sided adhesive, skin-compatible protective layer. The protective layer then has the first adhesive layer on the one side and the second adhesive layer on the opposite side. The first adhesive layer, the skin-compatible protective layer, and the second adhesive layer can be designed as one piece as, in particular, a double-sided adhesive, adhesive layer/protective layer composite.

Moreover, it is advantageous when the measuring device has an outer layer, which is arranged at a top side of the measuring device opposite the body during the use as intended. The outer layer can be designed, for example, as a textile layer, and so a wearing comfort of the measuring device is improved.

Moreover, it is advantageous when the measuring device includes a carrier unit, in which the measuring unit is arranged. Additionally or alternatively, the measuring unit can also be arranged on the carrier unit. Additionally or alternatively, the heat-conducting element can also be arranged in the carrier unit. Additionally or alternatively, the heat-conducting element can also be arranged on the carrier unit. The carrier unit can therefore accommodate the measuring unit and/or the heat-conducting element, in order to fix these, in particular, in the measuring device. The carrier unit can be designed, for example, in the shape of a disk, and so the measuring device is designed substantially in the shape of a disk. Moreover, the carrier unit can be made of a flexible and/or elastic material, and so the carrier unit and/or the measuring device can adapt to different body contours of the body to be measured. The carrier unit can be made, for example, of a flexible polymer material, for example, on the basis of carbon or silicon. The polymer material can be, for example, a plastic and/or a silicone. For example, the carrier unit can also be a printed circuit board, at which the measuring unit is arranged. The printed circuit board can include electrical lines. The printed circuit board can also be flexible. The measuring unit can be supplied, for example, with a voltage via the carrier unit. The carrier unit can also include an antenna, in order to be able to wirelessly transmit the measured body temperature. Moreover, if the carrier unit is the printed circuit board, the measuring unit can be soldered, for example, onto this. The measuring unit can also be connected to the antenna with the aid of the printed circuit board.

Moreover, it is advantageous when the heat-conducting element includes a planar element, which is arranged on a side of the measuring unit facing the body during the use of the measuring device as intended. The planar element is designed to be flat, and so the planar element has thermal contact with the body and/or with the skin of the living being in an appropriately large area. As a result, the heat flow of the heat-conducting element can be improved, and so, for example, the temperature difference between the measuring unit and the body can be equalized in a short time. Consequently, the body temperature can be measured appropriately quickly. The planar element can have direct contact with the measuring unit. The planar element can therefore be directly connected to the measuring unit. The planar element can therefore form a heat-conducting layer on the measuring unit. The planar element is therefore arranged at the measuring unit. The measuring unit and the planar element can also be designed as one piece. The planar element can be arranged, for example, at least partially in the measuring unit.

Moreover, it is advantageous when the heat-conducting element includes a lead. The lead can extend, for example, from the measuring unit to the side of the measuring device facing the body during the use as intended. The lead can extend, for example, up to the protective layer. The lead can extend, for example, through the carrier unit, and so the heat flow between the body and the measuring unit can be formed by the carrier unit. The carrier unit can include, for example, a contact-making opening, through which the lead extends, in particular, from the measuring unit toward the body. The heat flow between the body of the living being and the measuring unit can also be formed with the aid of the lead. The lead can also be arranged between the planar element and the measuring unit, and so the planar element is spaced apart from the measuring unit. As a result, the heat-conducting element includes at least the planar element and the lead. With the aid of the lead, for example, the measuring unit can be arranged so as to be spaced apart from the underside of the measuring device. The lead can therefore form the heat flow between the planar element and the measuring unit.

When the planar element has a larger cross-section than the lead, this also provides advantages. As a result, the lead has a flexibility, in particular, the lead can bend, and so the heat-conducting element, which includes the planar element and the lead, can adapt to the body contour. Since the lead is flexible, due to the smaller cross-section as compared to the planar element, the planar element can pivot, in order to adapt to the body contour. For example, the planar element should be oriented substantially in parallel to the body surface and/or to the skin in order to be able to form a high heat flow between the body and the measuring unit.

In addition, the heat flow can be increased with the planar element, since the heat flow also depends on the cross-sectional area of the planar element.

Additionally or alternatively, the flexibility of the lead can also be formed in that it has a certain shape. For example, the lead can have a constriction, and so the flexibility is formed.

Additionally or alternatively, the flexibility of the lead can also be achieved by way of the material selection of the lead. For example, the lead can be formed from a flexible material. Of course, the selection of the material should affect the thermal conductivity of the lead only slightly or in such a way that the functional capability of the measuring device is adversely affected only slightly or not at all.

Moreover, the lead can be formed from a material that is different from the planar element. For example, the lead can be made of a material that has a higher thermal conductivity as compared to the material of the planar element. As a result, for example, the smaller cross-section of the lead as compared to the planar element can be compensated for. Less consideration can be given to skin compatibility when selecting the material of the lead, since the lead can be located in an inner area of the measuring device. Consequently, a greater number of different materials is available, which, for example, have a greater thermal conductivity and/or are more cost-effective as compared to the planar element.

It is also advantageous when the protective layer extends completely across the underside of the measuring device. As a result, for example, an irritation by the measuring device is reduced. The underside faces the body during the use of the measuring device as intended. Additionally or alternatively, the adhesive layer can also extend completely across the underside of the measuring device. As a result, the measuring device securely adheres on the body.

It is advantageous when the protective layer includes, at least in the area of the heat-conducting element, at least one thermal contact element and/or additives, by means of which the heat flow can be increased. Additionally or alternatively, it is advantageous when the adhesive layer includes, at least in the area of the heat-conducting element, at least one thermal contact element and/or additives, by means of which the heat flow can be increased. The thermal contact element and/or the additives therefore increase the thermal conductivity, and so a temperature difference between the body of the living being and the measuring unit is more quickly equalizable. The thermal contact element can include, for example, particles made of a material, for example, metals such as silver, copper, etc., having high thermal conductivity. Such thermal contact elements can be admixed to the material of the protective layer. Additionally or alternatively, the additives can also include metals.

It is advantageous when the measuring device has a sealing. The sealing can enclose at least the measuring unit, the heat-conducting element, and/or the carrier unit. The sealing can also be, for example, a potting. The sealing can also be formed from a flexible material, and so the sealing can adapt to the body contour.

Additionally or alternatively, the sealing can be formed, for example, from at least one foam sheet, which can have at least one recess. The measuring unit, for example, can be arranged in the recess. The sealing can also be composed of multiple, for example, two foam sheets, which are arranged one above the other and encapsulate at least the measuring unit. One advantage of the foam sheet is that it is highly thermally insulating, and so a heat flow from the surroundings toward the measuring unit is reduced. As a result, the measurement is corrupted to a lesser extent by the surroundings.

Moreover, it is advantageous when the heat-conducting element is made from metal. Since metals mostly have good thermal conductivity, the heat-conducting element can be easily formed as a result. Another advantage of metal is that the heat-conducting element can be more easily manufactured. The heat-conducting element can be, for example, milled or cast. Additionally or alternatively, it is advantageous when the heat-conducting element is formed from a varnish. As a result, the heat-conducting element can be manufactured in a simple way when, for example, the heat-conducting element is applied on as varnish.

Additionally or alternatively, the lead and/or the planar element can also be designed as metal and/or varnish.

Moreover, it is advantageous when the measuring device has an energy unit. The energy unit can include, for example, a battery and/or an accumulator, which can supply the measuring device with electrical energy. Additionally or alternatively, the energy unit can also include a supercapacitor, which is charged and can store electrical energy for a longer time.

Additionally or alternatively, the measuring device can include a memory unit, by means of which the temperature measurement values of the measuring unit can be stored. As a result, the body temperature can be measured, for example, every hour, in order to create a temperature profile of the body temperature. As a result, an increase and/or a decrease of the body temperature can be detected. The measured values can therefore be intermediately stored until they are read out.

Additionally or alternatively, the measuring device can include an interface. The body temperature, for example, can be read out via the interface. An external read-out device, for example, can couple onto the interface, in order to read out the body temperature. For this purpose, the interface can be designed, for example, as an RFID interface. The interface can also be a Bluetooth, a WLAN, and/or a hard-wired interface or another type of interface. A smartphone, for example, can couple onto the interface, in order to read out the body temperature. The interface can also be an NFC (near field communication) interface.

Additionally or alternatively, the measuring device and/or the energy unit can also include an energy conversion unit. The energy conversion unit can include, for example, one or multiple piezoelectric element(s), which can convert a movement of the measuring device into electrical energy. As a result, the measuring device can be operated with the aid of the kinetic energy. Additionally or alternatively, the energy conversion unit can also include a Peltier element, which generates electrical energy from a temperature difference, with which the measuring device can be operated. Additionally or alternatively, the energy conversion unit can also include an inductive and/or capacitive unit, which converts an existing electrical and/or magnetic field into electrical energy, and so the measuring device can be operated.

It is also advantageous when the interface is designed in such a way that the energy for measuring the body temperature and/or the energy for reading out the body temperature is made available, for example, from a memory of the measuring unit, via the interface. For this purpose, the interface can be designed in such a way that it draws the electrical energy from an electromagnetic field, which is formed, for example, by the external read-out device, and, as a result, determines and/or can read out the body temperature. The read-out of the body temperature can also take place again by the external read-out device. This has the advantage that the energy store can be dispensed with and the measuring device can be more cost-effectively manufactured and is substantially unlimited with respect to service life. The interface can be, for example, the NFC interface.

It is also advantageous when the sealing and the protective layer are made of the same material. As a result, for example, the protective layer and the sealing can be designed as one piece.

It is also advantageous when the sealing is made of a foam and/or of a silicone. The foam can be, for example, a polyethylene foam. As a result, the sealing can be designed to be thermally insulating, in order to reduce a heat flow from the surroundings toward the measuring unit. For example, the sealing can be made of polyethylene or a polyethylene foam. The protective layer can be made, for example, of polyester.

The sealing can also be made of a foam sheet, in particular polyethylene foam sheet. The measuring unit can be encapsulated in the foam sheet.

It is advantageous when the sealing is made of a material, which has a lower thermal conductivity than a material of the protective layer. For this purpose, the sealing can be made, for example, of the foam. As a result, the body temperature is more quickly conducted to the measuring unit. The measuring unit therefore quickly adapts to the body temperature. Consequently, the body temperature can be measured faster. In contrast, an ambient temperature is conducted less well to the measuring unit, and so the measuring unit predominantly measures the body temperature.

Additionally or alternatively, it is advantageous when the protective layer is made of polyester. Additionally or alternatively, the protective layer can also be made of polyethylene.

Moreover, the sealing can be made of a silicone and the protective layer can be made of polyethylene or polyester. Since the protective layer is made of polyethylene or polyester, which has good thermal conductivity as compared to silicone, the measuring unit can quickly measure the body temperature.

Moreover, since the sealing, which can encapsulate the measuring unit, has a poorer thermal conductivity as compared to the protective layer, the measuring unit can be insulated with respect to the ambient temperature. As a result, the measuring unit measures the body temperature and not the ambient temperature. Consequently, the measuring accuracy of the body temperature is improved, since effects of the ambient temperature are reduced.

BRIEF DESCRIPTION OF THE DRAWINGS

Further advantages of the invention are described in the following exemplary embodiments. Wherein.

DETAILED DESCRIPTION OF EXEMPLARY EMBODIMENTS

Figure 1:
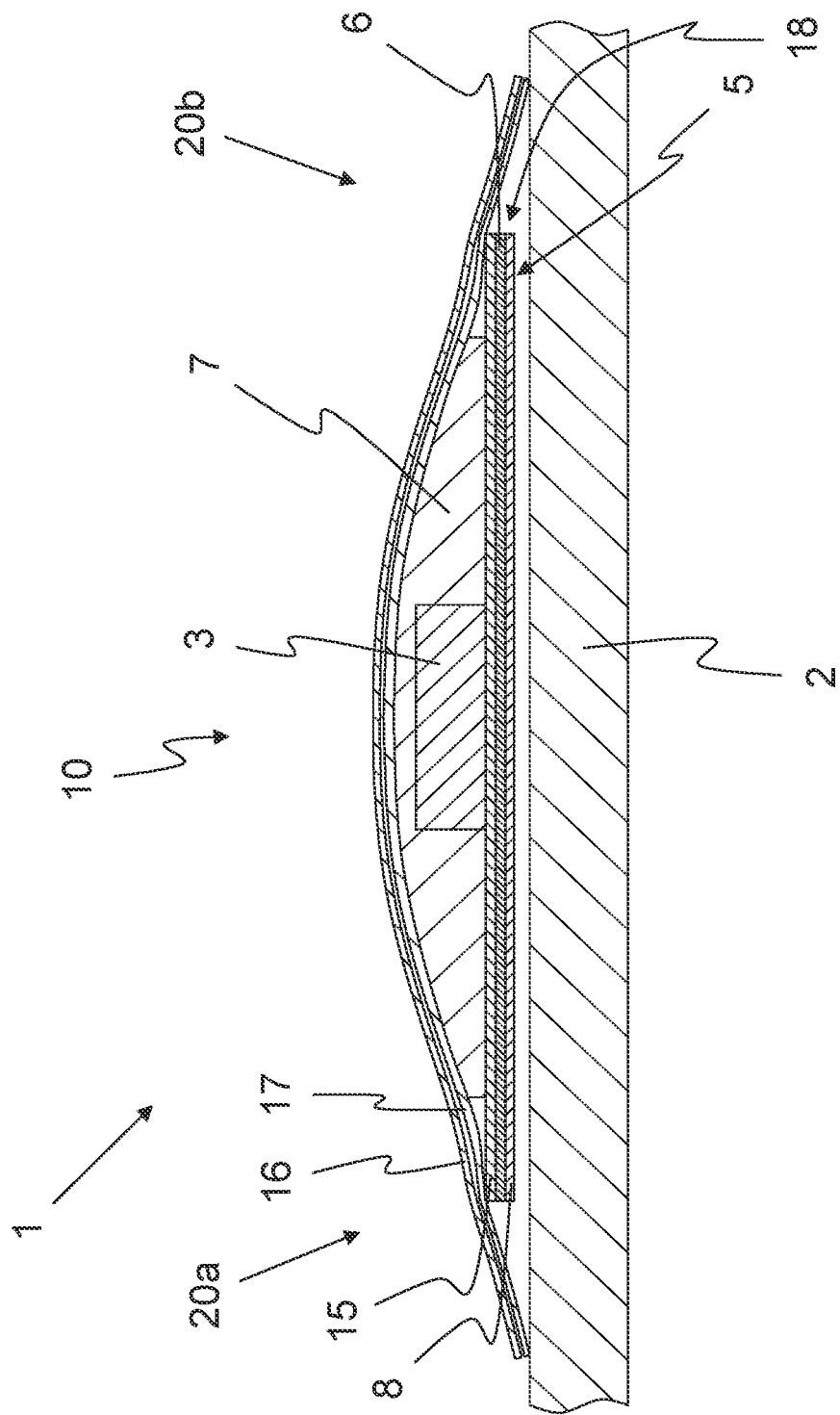
FIG. 1 shows a diagrammatic sectional view of a measuring device for measuring a body temperature with a measuring unit, an adhesive layer, and a protective layer.

FIG. 1 shows a diagrammatic view of a measuring device 1 for measuring a body temperature of a body 2 of a living being with a measuring unit 3, a first skin-compatible adhesive layer 8, and a skin-compatible protective layer 6. The measuring device 1 is represented spaced apart from the body 2 for the sake of clarity. When the measuring device 1 is used as intended, it advantageously has contact with the body 2.

The figures are not represented true to scale, for the sake of clarity. For example, the aforementioned adhesive layers 8, the protective layer 6, etc., are represented substantially thicker.

The body temperature of the body 2 can be measured and/or determined with the aid of the measuring unit 3. The body temperature can be measured, in that the measuring unit 3 itself assumes the body temperature during the contact with the body 2. In order to measure the temperature, the measuring unit 3 can include, for example, a sensor element (not shown here) and/or a temperature probe. For example, the measuring unit 3 can include a temperature-dependent diode and/or a temperature-dependent resistor, by means of which the body temperature is determinable. The measuring unit 3 can include a semiconductor sensor for determining the body temperature. Additionally, the measuring unit 3 can also include a processing unit (not shown here), by means of which the values detected by the measuring unit 3, the semiconductor sensor, the temperature-dependent diode, the sensor element, and/or the temperature probe can be converted into a temperature value. For example, the sensor element can include a temperature-dependent resistor, wherein the processing unit determines the temperature on the basis of the change of a current flow through the sensor element.

The body temperature of the body 2 can be measured, for example, in that the measuring unit 3 has the same temperature as the body 2.

Moreover, as shown in FIG. 1 for example, the measuring device 1 has an underside 5, which faces the body 2 and/or has contact thereto during the use of the measuring device 1 as intended. In addition, the measuring device 1 has a top side that is generally designated by the numeral 10, which faces away from the body 2 during the use of the measuring device 1 on the body 2 as intended.

Moreover, the measuring device 1 includes the skin-compatible protective layer 6. As shown in FIG. 1 for example, the skin-compatible protective layer 6 is arranged at a side of the measuring device 1 facing the body 2 intended therefor. The protective layer 6 can be arranged on the underside 5 or in the region of the underside 5 of the measuring device 1. When the measuring device 1 is arranged at the body 2 in order to measure the body temperature, the skin-compatible protective layer 6 is arranged between the measuring unit 3 and the body 2 or the skin (not shown here) of the body 2. Therefore, the measuring unit 3 can be spaced apart from the body 2 during the use of the measuring device 1 as intended. Direct contact between the body 2 and the measuring unit 3 can therefore be prevented. As a result, for example, there is no need to ensure that the measuring unit 3 itself is skin-compatible. For example, the measuring unit 3 can be designed as a semiconductor chip. The material of the measuring unit 3 and/or the measuring unit 3 itself does not need to be tested to determine whether it is injurious to health or irritating to the skin. By means of the skin-compatible protective layer 6, untested measuring units 3 can also be utilized, since the protective layer 6 encapsulates the measuring unit 3 and/or prevents direct contact of the measuring unit 3 with the body 2.

Moreover, the protective layer 6 can be designed as a liquid and/or gas diffusion barrier. As a result, for example, corrosion of the measuring unit 3 can be prevented.

Moreover, the protective layer 6 can be designed, for example, to be water-tight, and so penetration of moisture into the measuring device 1 can be prevented. Additionally or alternatively, the protective layer 6 can also have a seal tightness for gases or be gas-tight, and so, for example, gases arising from a degassing of materials of the measuring device 1 do not come into contact with the body 2.

According to the present exemplary embodiment from FIG. 1, the protective layer 6 is arranged at the underside 5 of the measuring device 1.

Moreover, the protective layer 6 can have a thickness, which only slightly affects the heat flow or the thermal conduction between the body 2 and the measuring unit 3. For example, the protective layer 6 has a thickness, which is in the range between 0.001 mm and 1 mm. The thickness can also be in a range between 25 µm and 500 µm. The thickness of the protective layer 6 can also be 50 µm, however. The protective layer 6 should be as thin as necessary so that the measuring unit 3 can measure the body temperature well.

Moreover, as shown in FIG. 1 for example, the measuring device 1 has a first adhesive layer 8. With the aid of the adhesive layer 8, the measuring device 1 can be fastened on the body 2 and/or on the skin of the body 2, and so the body temperature of the body 2 can be determined, for example, over a longer time period and, as a result, changes in the body temperature can also be determined.

The first adhesive layer 8 is arranged at the side of the measuring device 1 facing the body 2 during the use of the measuring device 1 as intended as shown in FIG. 1 for example. The first adhesive layer 8 is arranged at the underside 5 of the measuring device 1. The skin-compatible protective layer 6 is arranged between the first adhesive layer 8 and the measuring unit 3. The first adhesive layer 8 extends in a planar manner across the underside 5 of the measuring device 1, and so the measuring device 1 can be securely arranged on the body 2. Moreover, the first adhesive layer 8 can extend completely across the skin-compatible protective layer 6. The first adhesive layer 8 can have, for example, channels, in order to be able to transport away sweat between the body 2 and the measuring device 1. The measuring device 1 can include a drainage system (not shown here) in the first adhesive layer 8, in order to drain away the sweat between the body 2 and the measuring device 1. This drainage system can be formed by the channels defined in the first adhesive layer 8.

According to the present exemplary embodiment as shown in FIG. 1 for example, the measuring device 1 has a second adhesive layer 15. The second adhesive layer 15 is arranged between the skin-compatible protective layer 6 and the measuring unit 3. As a result, the skin-compatible protective layer 6 can be connected to the measuring unit 3. The skin-compatible protective layer 6 is arranged between the first adhesive layer 8 and the second adhesive layer 15.

The first adhesive layer 8, the skin-compatible protective layer 6, and the second adhesive layer 15 can be designed as a double-sided adhesive, skin-compatible protective layer. The first adhesive layer 8, the skin-compatible protective layer 6, and the second adhesive layer 15 can therefore be designed as one piece. For example, the first adhesive layer 8 and the second adhesive layer 15 can be applied onto the skin-compatible protective layer 6. The first adhesive layer 8, the skin-compatible protective layer 6, and the second adhesive layer 15 can have the form of a double-sided, skin-compatible adhesive tape. The first adhesive layer 8, the skin-compatible protective layer 6, and the second adhesive layer 15 can form an adhesive-protective layer composite 18, which can be designed as one integrated piece.

Moreover, the protective layer 6 and/or the adhesive layer 8 can form a planar surface, and so these can be placed completely on the body 2.

In addition, the measuring device 1 can have a sealing 7, which is made, for example, of a plastic foam. The sealing 7 can also be a potting. With the aid of the sealing 7, the measuring unit 3 can be sealed or potted. As a result, the measuring unit 3 is protected against damage, gases, and/or moisture from outside the measuring device 1. The measuring unit 3 is therefore encapsulated, and so the sealing 7 can also be an encapsulation. The sealing 7 can be made of a flexible material, and so the sealing 7 and, thereby, the measuring device 1 can adapt to a surface contour of the body 2.

The sealing 7 can completely enclose the measuring unit 3. The sealing 7 can be made, for example, of at least one foam sheet. Moreover, the foam sheet can have at least one recess, in which at least the measuring unit 3 and/or a battery as the energy unit 13 can be arranged. The foam sheet can be made, for example, of polyethylene foam.

It is advantageous when the sealing 7 is thermally insulating and the protective layer 6 and/or the first adhesive layer 8 are/is heat-conducting. In particular, the protective layer 6 and/or the first adhesive layer 8 have/has a greater thermal conductivity than the sealing 7.

The sealing 7 can also be made of a foam, in particular a polyethylene foam. Moreover, the protective layer 6 can be made of polyester. Such a material combination is advantageous, since polyester has better thermal conductivity as compared to the foam, in particular the polyethylene foam. It is also advantageous that the foam, in particular the polyethylene foam, has poorer thermal conductivity as compared to the polyester. The protective layer 6 made of polyester can quickly conduct the body temperature to the measuring unit 3. Consequently, the measuring unit 3 can quickly measure the body temperature.

In addition, the measuring unit 3 is insulated with respect to an ambient temperature by the sealing 7 made of the foam, in particular the polyethylene foam. The sealing 7 is, therefore, an insulation layer. As a result, the measuring unit 3 does not measure the ambient temperature, but rather the body temperature. A measuring accuracy of the measurement of the body temperature is improved as a result.

Additionally or alternatively, the first adhesive layer and/or the second adhesive layer can be made of an acrylates copolymer, and so these also have good thermal conductivity as compared to the foam. As a result, the first adhesive layer and/or the second adhesive layer also hardly impede(s) the measurement of the body temperature.

Additionally or alternatively, the first adhesive layer 8 and/or the second adhesive layer 15 are/is designed to be as thin as possible, for example, between 5 µm and 100 µm. Consequently, the thermal conduction between the body 2 and the measuring unit 3 is impeded as little as possible.

The first adhesive layer 8, the protective layer 6, and/or the second adhesive layer 15 extend, according to the present exemplary embodiment as shown in FIG. 1 for example, completely across the measuring unit 3 and/or the sealing 7. According to the present exemplary embodiment as shown in FIG. 1 for example, the first adhesive layer 8, the protective layer 6, and/or the second adhesive layer 15 extend laterally beyond the measuring unit 3 and/or the sealing 7.

According to the present exemplary embodiment as shown in FIG. 1 for example, two edge areas generally indicated by the numerals 20a, 20b are shown. The edge areas 20a, 20b can also extend completely around the measuring unit 3 and/or the sealing 7, and so the edge areas 20a, 20b are connected to each other and merge into one another.

According to the present exemplary embodiment, the measuring device 1 has an outer adhesive layer 17. This is arranged on the side of the measuring device 1 facing away from the body 2 during the use of the measuring device 1 as intended. The outer adhesive layer 17 is therefore arranged at the top side 10 of the measuring device 1 as shown in FIG. 1 for example. The outer adhesive layer 17 can encapsulate at least the measuring unit 3 with respect to the surroundings of the measuring device 1. The outer adhesive layer 17 can be designed, for example, similarly to the adhesive-protective layer composite 18. In particular, the outer adhesive layer 17 can include a skin-compatible protective layer and at least one, in particular two adhesive layer(s). The outer adhesive layer 17 and the adhesive-protective layer composite 18 and/or the second adhesive layer 15 can be adhesively bonded to each other, in particular, in their edge areas 20a, 20b, and so the measuring unit 3 is completely encapsulated. As shown here, the edge areas 20a, 20b extend laterally away, and so these at least partially, in particular completely, border the measuring unit 3 and/or the sealing 7.

For example, as shown in FIG. 1 for example, the outer adhesive layer 17 can be adhesively bonded together with the second adhesive layer 15, and so these two adhesive layers 15, 17 encapsulate at least the measuring unit 3 and/or the sealing 7. For example, the outer adhesive layer 17 can be adhesively bonded together with the second adhesive layer 15 in edge areas 20a, 20b.

According to the present exemplary embodiment as shown in FIG. 1 for example, the measuring device 1 has an outer layer 16, which can be designed, for example, as a textile layer. The outer layer 16 can be adhesively bonded, for example, onto the outer adhesive layer 17. A wearing comfort of the measuring device 1 can be improved with the aid of the outer layer 16. Moreover, the outer layer 16 can extend, in particular in a transverse direction of the measuring device 1, beyond the adhesive-protective layer composite 18, the first adhesive layer 8, the skin-compatible protective layer 6, the second adhesive layer 15, and/or the outer adhesive layer 17.

According to the present exemplary embodiment as shown in FIG. 1 for example, the outer adhesive layer 17 is arranged completely on the underside of the outer layer 16. As a result, the outer layer 16 can be adhesively bonded onto the body 2 with the aid of the outer adhesive layer 17. As a result, the measuring device 1 is securely adhesively bonded onto the body 2 with the aid of the outer adhesive layer 17. The outer layer 16 is also adhesively bonded at the body 2 with the aid of the outer adhesive layer 17.

The outer layer 16 and the outer adhesive layer 17 can form a textile-adhesive composite.

In the present exemplary embodiment as shown in FIG. 1 for example, the outer layer 16 and the outer adhesive layer 17 extend beyond the protective layer 6 and/or the first adhesive layer 8. Alternatively, the outer layer 16, the outer adhesive layer 17, and the protective layer 6 and/or the first adhesive layer 8 can be flush with one another. The outer layer 16, the outer adhesive layer 17, and the protective layer 6 and/or the first adhesive layer 8 can therefore terminate in the edge areas 20a, 20b in a flush manner. The outer layer 16, the outer adhesive layer 17, and the protective layer 6 and/or the first adhesive layer 8 are connected to each other in the edge areas 20a, 20b. In the edge areas 20a, 20b, the measuring device 1 can be adhesively bonded on the body 2 in a planar manner. The edge areas 20a, 20b can then form a barrier for water and/or moisture. The edge areas 20a, 20b, when adhesively bonded on the body 2, can prevent water or moisture and, in particular, dirt, from entering the area between the measuring unit 3 and the body 2.

Alternatively, in the edge areas 20a, 20b, the outer layer 16 and/or the outer adhesive layer 17 can also protrude laterally beyond the protective layer 6, the first adhesive layer 8 and/or the second adhesive layer 15. The outer adhesive layer 17 and/or the outer layer 16 therefore adhesively bond(s) directly onto the body 2. Moreover, it is advantageous when the outer layer 16 and/or the outer adhesive layer 17 are/is air-permeable and/or water-permeable, and so, as a result, sweat, for example, can evaporate in these areas, in particular in the edge areas 20a, 20b, and so wearing comfort is improved.

As shown here in FIG. 1 for example, the outer adhesive layer 17 and the second adhesive layer 15 overlap, at least in some areas, in the edge areas 20a, 20b. There, the two layers 15, 17 are adhesively bonded together, and so at least the measuring unit 3 and/or the sealing 7 are/is encapsulated. In addition, as a result, a connection with the protective layer 6, the first adhesive layer 8, and the second adhesive layer 15 to the outer adhesive layer 17 and the outer layer 16 is ensured.

When the outer layer 16, the outer adhesive layer 17, and the protective layer 6 and/or the first adhesive layer 8 are connected to each other, this has the advantage, consequently, that the measuring unit 3, the sealing 7, a carrier unit 9, a heat-conducting element 11, an energy unit 13, and/or an interface 14 are/is encapsulated. The outer layer 16, the outer adhesive layer 17, and the protective layer 6 and/or the first adhesive layer 8 therefore form a casing for at least the measuring unit 3 and/or the sealing 7.

Figure 2:
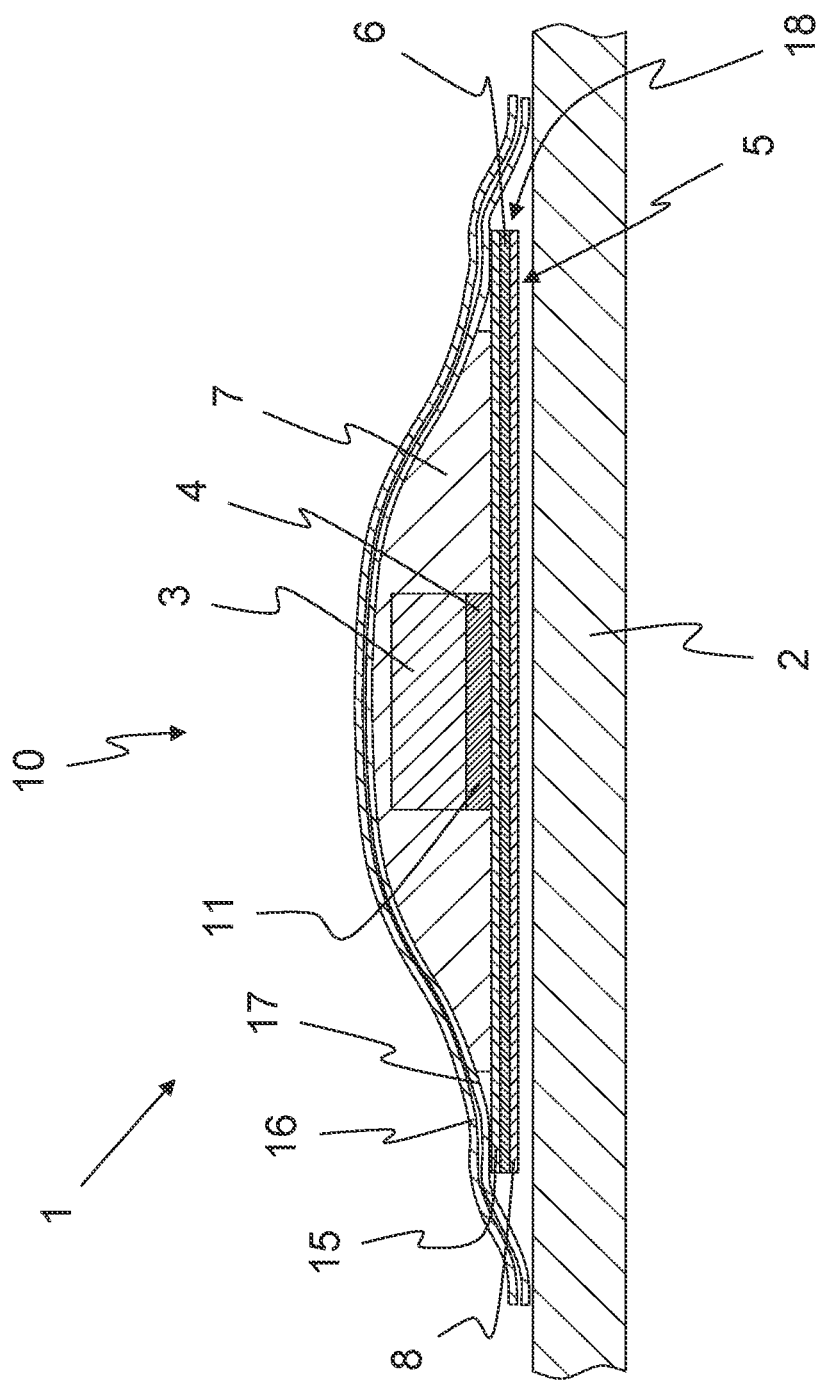
FIG. 2 shows a diagrammatic sectional view of a measuring device for measuring a body temperature with a measuring unit and a heat-conducting element.

FIG. 2 shows a diagrammatic sectional view of a measuring device 1 with the measuring unit 3, a heat-conducting element 4, the protective layer 6, and the first adhesive layer 8.

Features that have already been described with reference to the preceding figures are not described once more, for the sake of simplicity. Moreover, identical reference numerals are utilized for identical or at least similar features. For the sake of simplicity, features can also be described first initially in one or several of the following figures. Identical reference numerals are also utilized in the following figures for identical or similar features.

The measuring device 1 shown in FIG. 2 for example includes the heat-conducting element 4 in order to adapt the temperature of the measuring unit 3 to the body temperature of the body 2, and so the body temperature can be determined by the measuring unit 3. A heat flow can be formed between the body 2 and the measuring unit 3 by means of the heat-conducting element 4. The heat flow can be formed bidirectionally between the measuring unit 3 and the body 2.

If, for example, the body 2 has a higher temperature than the measuring unit 3, then the heat-conducting element 4 conducts heat from the body 2 to the measuring unit 3 until the temperatures have equalized.

However, if the body 2 has a lower temperature than the measuring unit 3, then the heat-conducting element 4 conducts heat from the measuring unit 3 to the body 2 until the temperatures have equalized.

Once the temperatures have equalized, then the body temperature of the body 2 can be determined.

The heat-conducting element 4 as shown in FIG. 2 for example is designed to be planar here. The heat-conducting element 4 can include a planar element 11. The heat-conducting element 4 can be designed as a planar element 11. The body temperature can be quickly measured by the heat-conducting element 4 and/or the planar element 11, since the heat can be quickly exchanged between the measuring unit 3 and the body 2.

Figure 3:
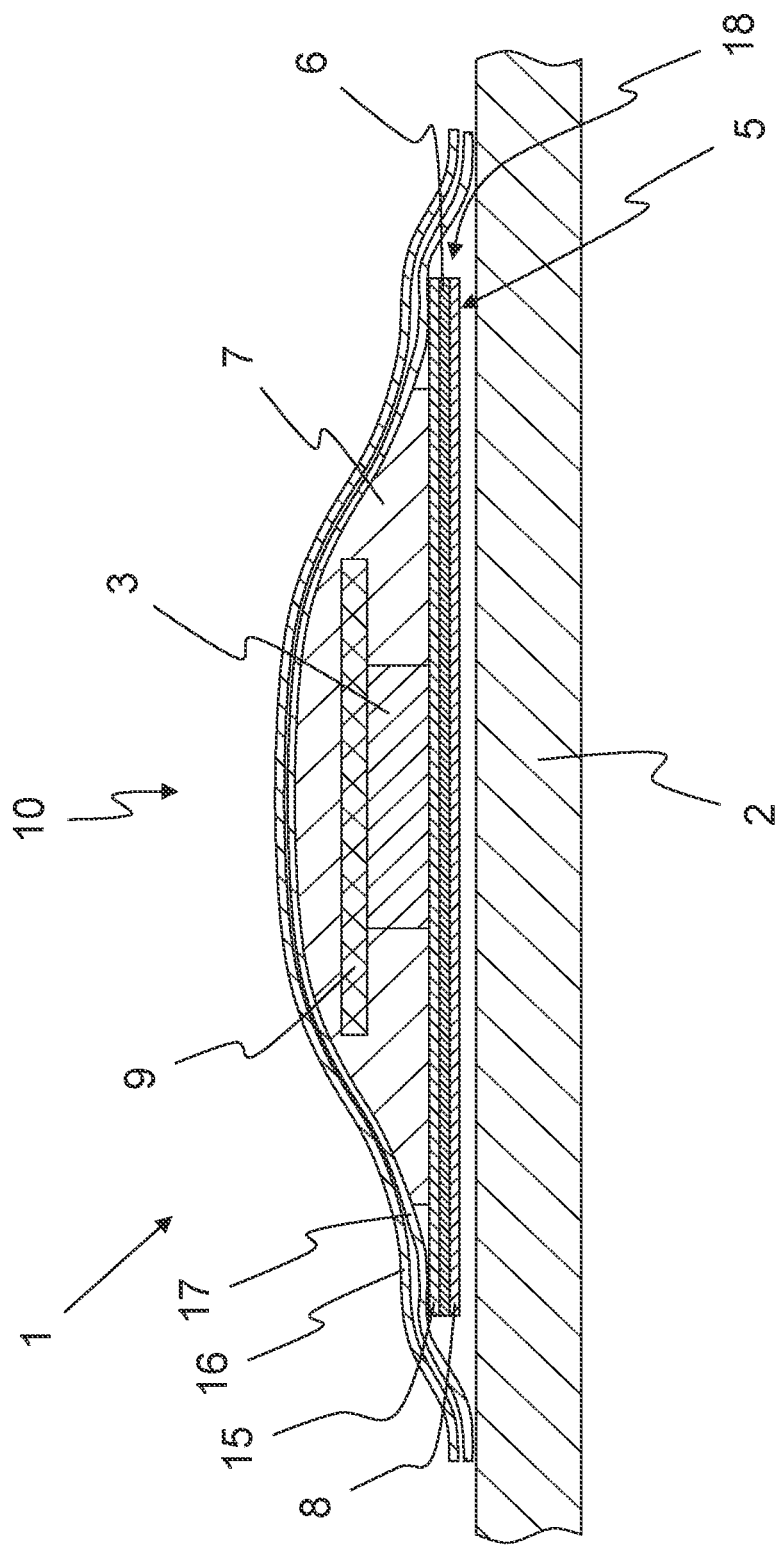
FIG. 3 shows a diagrammatic sectional view of a measuring device for measuring a body temperature with a carrier unit.

FIG. 3 shows a measuring device 1 with a carrier unit 9. The carrier unit 9 can be, for example, a printed circuit board, which is preferably designed to be flexible. The printed circuit board can include strip conductors, wherein the measuring unit 3 is electrically conductively connected to the printed circuit board. The printed circuit board can supply, for example, the measuring unit 3, with electrical energy. Additionally or alternatively, the measured values of the body temperature can be conducted by the heat connection element to the printed circuit board to an interface, for example, an antenna, and so the measured values of the body temperature can be evaluated by an external read-out unit.

Features that have already been described in one of the preceding figures are not described once more, for the sake of simplicity. Moreover, identical reference numerals are utilized for identical or at least similar features. For the sake of simplicity, features can also be described first in one or several of the following figures. Identical reference numerals are also utilized in the following figures for identical or similar features.

The measuring unit 3 in the present exemplary embodiment shown in FIG. 3 for example is arranged at the side of the carrier unit 9 facing the body 2 during the use as intended.

The carrier unit 9 can also form a basic structure for the measuring device 1.

With the aid of the carrier unit 9, the measuring device 1 can be designed to be more stable. The carrier unit 9 can be made of a flexible material, and so the carrier unit 9 can adapt to the body contour. The carrier unit 9 can be made, for example, of an elastic plastic.

In the present exemplary embodiments, the measuring unit 3 and the carrier unit 9 are completely enclosed by the sealing 7.

Figure 4:
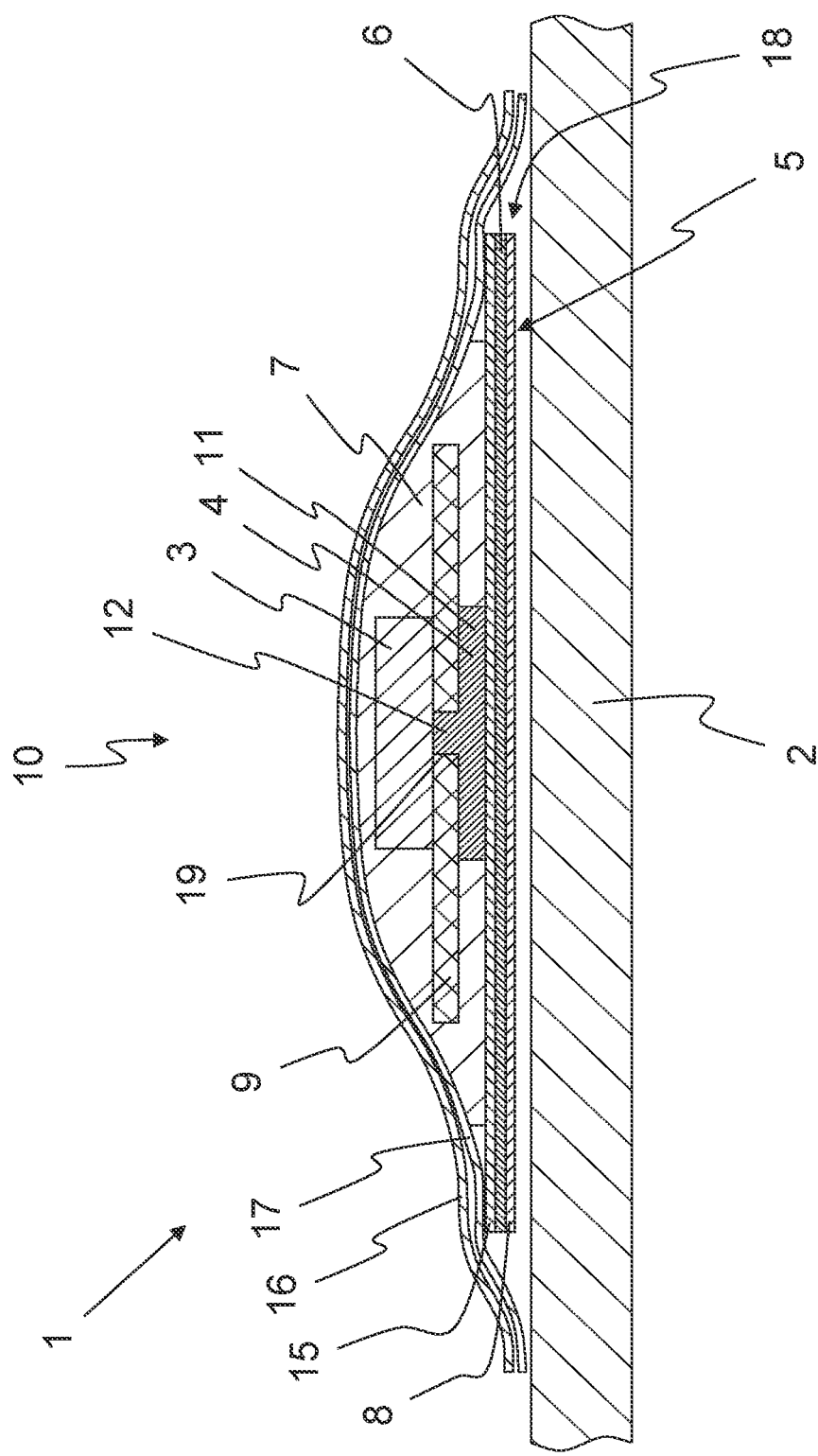
FIG. 4 shows a diagrammatic sectional view of a measuring device for measuring a body temperature with a carrier unit and a heat-conducting element.

FIG. 4 shows a measuring device 1 with the carrier unit 9 and a heat connection element or lead 12. Features that have already been described in one of the preceding figures are not described once more, for the sake of simplicity. Moreover, identical reference numerals are utilized for identical or at least similar features. For the sake of simplicity, features can also be described first in one or several of the following figures. Identical reference numerals are also utilized in the following figures for identical or similar features.

In the present exemplary embodiment shown in FIG. 4 for example, the measuring unit 3 is arranged on the side of the carrier unit 9 facing away from the body 2 during the use of the measuring device 1 as intended. The measuring device 1 includes the heat-conducting element 4, which, in this exemplary embodiment, has the planar element 11, which is arranged on the side of the carrier unit 9 facing away from the measuring unit 3. Moreover, the heat-conducting element 4 includes a heat connection element or lead 12, which extends from the planar element 11 through the carrier unit 9 to the measuring unit 3. The carrier unit 9 can include a contact-making opening 19, through which the heat connection element or lead 12 extends. The contact-making opening 19 can have, for example, a round cross-section. The heat flow through the carrier unit 9 can be formed with the aid of the heat connection element or lead 12. As a result of the heat conducting pathway provided by the lead 12, the measuring unit 3 can be arranged on the one side of the carrier unit 9 and the planar element 11 can be arranged on the side of the carrier unit 9 opposite thereto.

In the present exemplary embodiment of FIG. 4, the heat-conducting element 4 includes the heat connection element or lead 12. The heat connection element or lead 12 extends through the carrier unit 9. Moreover, the heat connection element or lead 12 extends from the measuring unit 3 to the protective layer 6, in order to form the heat flow pathway between the body 2 and the measuring unit 3.

As shown in this exemplary embodiment from FIG. 4, additionally or alternatively, the heat-conducting element 4 can also include the planar element 11. The heat-conducting element 4 can therefore include the heat connection element or lead 12 and the planar element 11. The heat connection element or lead 12 therefore extends from the measuring unit 3, through the carrier unit 9, to the planar element 11. The heat connection element or lead 12 is arranged between the measuring unit 3 and the planar element 11. The heat connection element or lead 12 further conducts the heat from the planar element 11 to the measuring unit 3 when the body temperature is higher than the temperature of the measuring unit 3. Alternatively, the heat connection element or lead 12 can conduct the heat from the measuring unit 3 to the planar element 11 when the body temperature of the body 2 is lower than the temperature of the measuring unit 3.

Moreover, the measuring unit 3, the heat connection element or lead 12, and/or the planar element 11 can be arranged at the carrier unit 9, and so the measuring device 1 is more stable overall. Additionally or alternatively, the heat-conducting element 4 can also be arranged at the carrier unit 9.

Additionally or alternatively, the sealing 7 can also be connected to the carrier unit 9, and so the measuring device 1 is more stable overall. According to the present exemplary embodiment shown in each of FIGS. 3-6 for example, the sealing 7 can be arranged at least partially around the carrier unit 9.

According to the present exemplary embodiment shown in FIG. 4 for example, the heat connection element or lead 12 has a smaller cross-section than the planar element 11.

Figure 5:
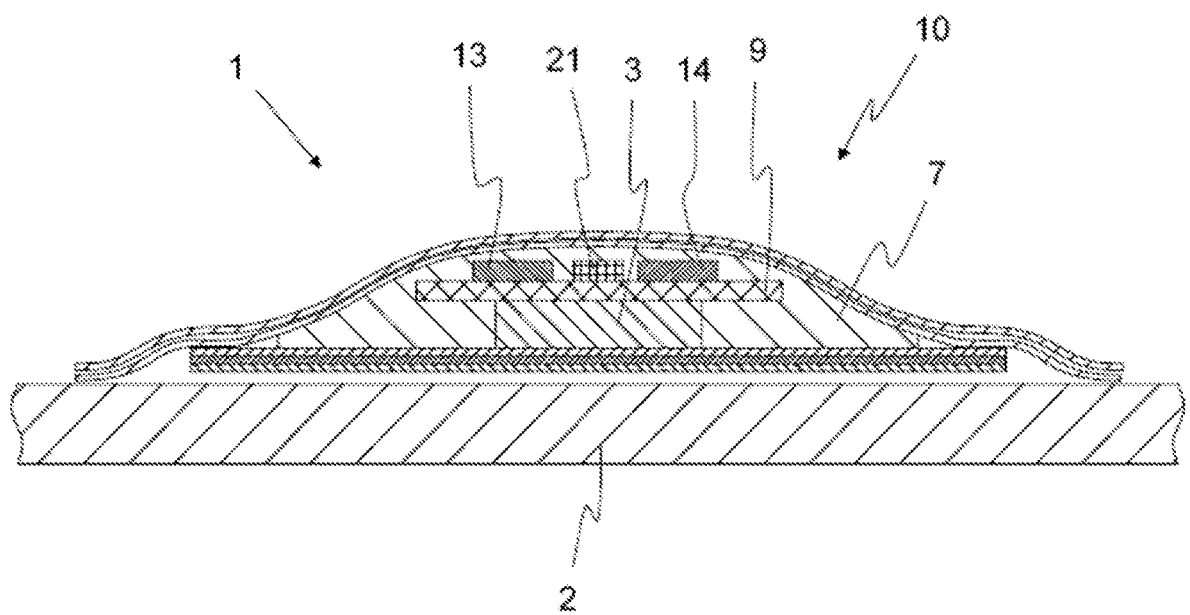
FIG. 5 shows a diagrammatic sectional view of a measuring device for measuring a body temperature with an energy unit and an interface.

FIG. 5 shows a diagrammatic sectional view of a measuring device 1 for measuring a body temperature, with an energy unit 13, a memory unit 21 and an interface 14. In the figure shown here, only the most important and new features are provided with a reference numeral. Features that have already been described in one of the preceding figures are not described once more, for the sake of simplicity. Moreover, identical reference numerals are utilized for identical or at least similar features. For the sake of simplicity, features can also be described first in one or several of the following figures. Identical reference numerals are also utilized in the following figures for identical or similar features.

The energy unit 13 can include, for example, a battery, an accumulator, and/or a supercapacitor, with which at least the measuring unit 3 can be supplied with electrical energy. The energy unit 13 can, however, also include a piezoelectric element which also generates electrical energy when the measuring device 1 moves, for example bends, on the body 2. The energy unit 13 can also include a Peltier element, however, which generates electrical energy from a temperature difference, in particular between the body 2 and a top side 10 of the measuring device 1. Additionally or alternatively, the energy unit 13 can include a capacitive and/or inductive unit, which generates electrical energy from an electric and/or magnetic field.

Additionally or alternatively, the measuring device 1 includes the interface 14, by means of which the determined body temperature of the body 2 can be, for example, read out. The interface 14 can include, for example, an antenna unit (not shown here), by means of which the body temperature can be read out wirelessly. A suitable read-out device, for example, can couple onto the interface 14, in order to read out the body temperature. A suitable example of the interface 14 includes an RFID interface. The interface 14 can also be based on NFC technology (near field communication).

The energy unit 13 and/or the interface 14 can be connected to the measuring unit 3, for example, by means of the carrier unit 9. It is advantageous when the carrier unit 9 is designed, in particular, as a flexible printed circuit board, which can form the electrical connection between the measuring unit 3 and the energy unit 13 and/or the interface 14.

The diagrammatic sectional views shown in the figures are not represented true to scale. For example, the layer thicknesses of the protective layer 6, the first adhesive layer 8, the second adhesive layer 15, the outer layer 16, and/or the outer adhesive layer 17 can be designed to be thinner, of course, in particular in relation to the measuring device 1.

Moreover, all electrical components, such as, for example, the measuring unit 3, the energy unit 13, the memory unit 21 and/or the interface 14, can be encapsulated by a varnish, which is water-tight and/or gas-tight. Moreover, the varnish can form a high liquid and/or gas diffusion barrier.

Figure 6:
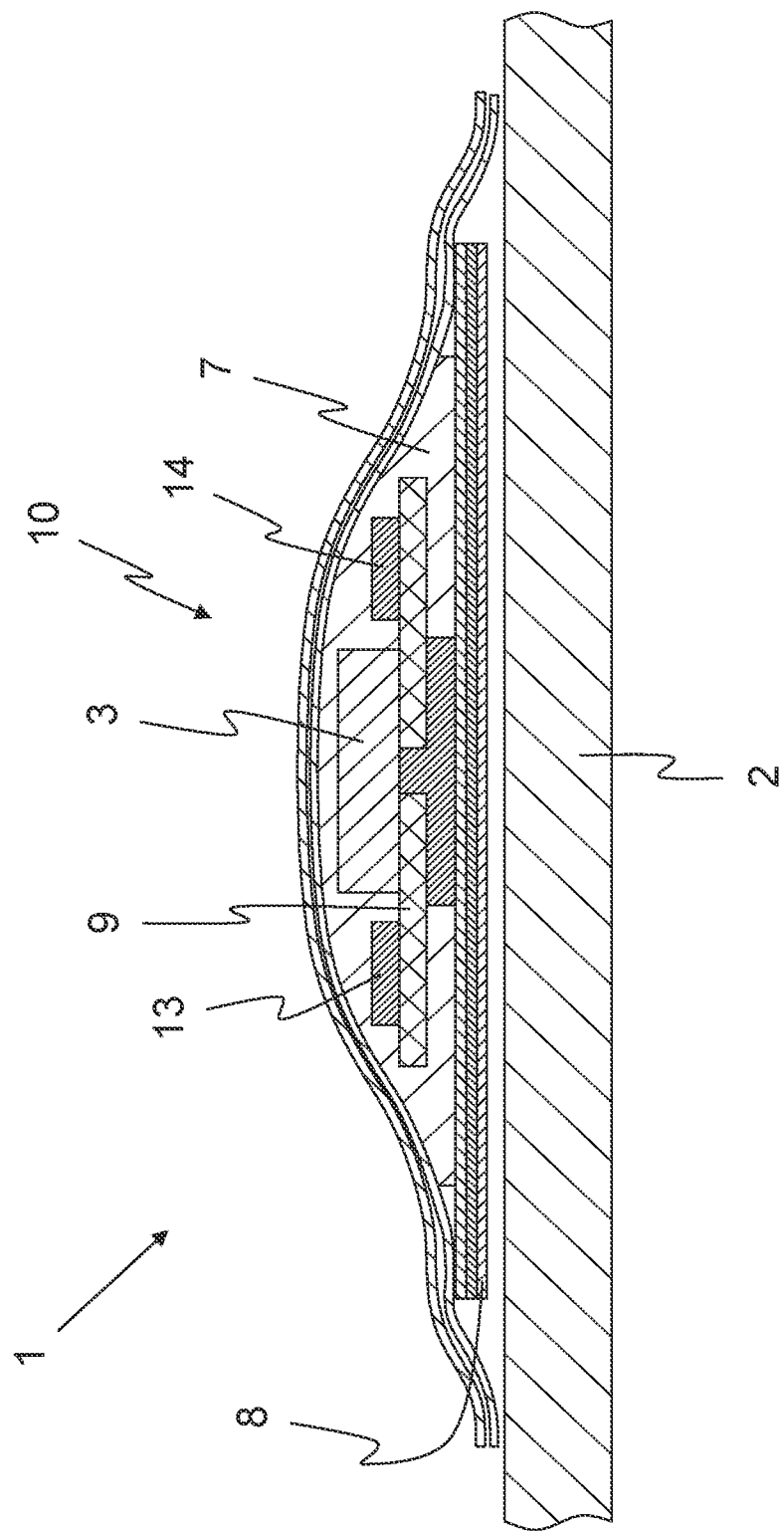
FIG. 6 shows a diagrammatic sectional view of a measuring device for measuring a body temperature with an energy unit and an interface.

FIG. 6 shows a diagrammatic exemplary embodiment of a measuring device 1 with a measuring unit 3, an energy unit 13, and/or the interface 14.

Features that have already been described in one of the preceding figures are not described once more, for the sake of simplicity. Moreover, identical reference numerals are utilized for identical or at least similar features. For the sake of simplicity, features can also be described first in one or several of the following figures. Identical reference numerals are also utilized in the following figures for identical or similar features.

For the sake of simplicity, only the features that are most important for the purpose of understanding are provided with a reference numeral. According to the present exemplary embodiment shown in FIG. 6 for example, the energy unit 13 and/or the interface 14 are/is arranged with the measuring unit 3 on the side of the carrier unit 9 facing away from the first adhesive layer 8. At least the carrier unit 9 is arranged between the energy unit 13, the interface 14, and/or the measuring unit 3 and the first adhesive layer 8. As a result, the distance between the energy unit 13 and/or the interface 14 and the measuring unit 3 is minimized, and so electrical lines between the measuring unit 3 and the energy unit 13 and/or the interface 14 are kept short. For example, the energy unit 13 and/or the interface 14 can be in direct contact with the measuring unit 3. When the energy unit 13 and/or the interface 14 and the measuring unit 3 are arranged on one side of the carrier unit 9, this provides a further advantage. When the carrier unit 9 includes printed lines or is designed as a printed circuit board itself, then the electrical printed lines can be arranged on only one side. As a result, the carrier unit 9 can be simplified when it includes electrical lines or is designed as a printed circuit board.

According to the present exemplary embodiment shown in FIG. 6 for example, the carrier unit 9, the measuring unit 3, the energy unit 13, and the interface 14 are completely enclosed by the sealing 7.

The present invention is not limited to the represented and described exemplary embodiments. Modifications within the scope of the claims are also possible, as is any combination of the features, even if they are represented and described in different exemplary embodiments.

LIST OF REFERENCE NUMERALS 1 measuring device
2 body
3 measuring unit
4 heat-conducting element
5 underside of the measuring device
6 protective layer
7 sealing
8 first adhesive layer
9 carrier unit
10 top side of the measuring device
11 planar element
12 heat connection element or lead
13 energy unit
14 interface
15 second adhesive layer
16 outer layer
17 outer adhesive layer
18 adhesive-protective layer composite
19 contact-making opening
20 edge areas
21 memory unit

The invention claimed is:

1. A measuring device for measuring a body temperature of a living being, the measuring device defining an underside facing the body when the measuring device is deployed for its intended use, the measuring device comprising:
   a measuring unit configured for measuring the body temperature,
   a first adhesive layer configured for fastening the measuring unit to the body of the living being, wherein the first adhesive layer (8) is arranged at a side of the measuring unit facing the body when the measuring device is deployed for its intended use,
   a skin-compatible protective layer, which is arranged between the first adhesive layer and the measuring unit;
   a heat-conducting element arranged between the skin-compatible protective layer and the measuring unit and configured for conducting a heat flow between the body of the living being and the measuring unit during the use of the measuring device as intended;
   a carrier unit, wherein the measuring unit and/or the heat-conducting element are/is arranged in and/or at the carrier unit;
   wherein the heat-conducting element includes a planar element, which is arranged on a side of the measuring unit facing the body during the use of the measuring device as intended, and wherein the heat-conducting element includes a lead;
   wherein the lead extends through the carrier unit and wherein the lead is arranged between the planar element and the measuring unit;
   an outer adhesive layer, wherein the measuring unit, the heat-conducting element and the carrier unit are arranged between the outer adhesive layer and the skin-compatible protective layer; and
   an outer layer, wherein the outer layer is adhesively bonded onto the outer adhesive layer and wherein the outer layer extends over the first adhesive layer and/or the skin-compatible protective layer.

2. The measuring device of claim 1, wherein the heat-conducting element includes a planar element, which is arranged on a side of the measuring unit facing the body during the use of the measuring device as intended.

3. The measuring device of claim 2, wherein the heat-conducting element includes a lead, which is arranged between the planar element and the measuring unit, and wherein the planar element is spaced apart from the measuring unit.

4. The measuring device of claim 3, wherein the planar element has a larger cross-section than the lead.

5. The measuring device of claim 1, wherein the protective layer, the first adhesive layer and/or the second adhesive layer extend(s) completely across the underside of the measuring device facing the body during the use as intended.

6. The measuring device of one of the claim 1, wherein the protective layer and/or the adhesive layer include(s), at least in the region of the heat-conducting element, at least one thermal contact element and/or additives, by means of which heat flow between the heat-conducting element and the measuring unit can be increased.

7. The measuring device of claim 1, further comprising a sealing, which encloses the measuring unit.

8. The measuring device of claim 7, wherein the sealing and the protective layer are made of the same material.

9. The measuring device of claim 4, wherein the lead and/or the planar element are/is made of metal.

10. The measuring device of claim 1, further comprising an energy unit, a memory unit and/or interface, which are arranged in and/or at the carrier unit.

11. The measuring device of claim 7, wherein the sealing is made of a foam.

12. The measuring device of claim 1, further comprising a sealing, which encloses the heat-conducting element.

13. The measuring device of claim 1, further comprising a sealing, which encloses the carrier unit.

14. The measuring device of claim 1, further comprising a sealing, which encloses the measuring unit and the heat-conducting element.

15. The measuring device of claim 1, further comprising a sealing, which encloses the measuring unit and the carrier unit.

16. The measuring device of claim 1, further comprising a sealing, which encloses the heat-conducting element and the carrier unit.

17. The measuring device of claim 1, further comprising a sealing, which encloses the measuring unit, the heat-conducting element, and the carrier unit.

18. The measuring device of claim 4, wherein the lead and/or the planar element are/is made of varnish.

19. The measuring device of claim 1, further comprising an energy unit, a memory unit and/or interface, which are arranged in and/or at the measuring unit.

20. The measuring device of claim 7, wherein the protective layer is made of polyester and/or polyethylene.

* * * * *